United States Patent
Qing et al.

(10) Patent No.: US 11,656,757 B2
(45) Date of Patent: May 23, 2023

(54) MONITOR AND DISPLAY SCREEN SWITCHING METHOD THEREFOR

(71) Applicants: SHENZHEN MINDRAY BIO-MEDICAL ELECTRONICS CO., LTD., Shenzhen (CN); Shenzhen Mindray Scientific Co., Ltd., Shenzhen (CN)

(72) Inventors: Lei Qing, Shenzhen (CN); Shuaijun Liu, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

(*) Notice: Subject to any disclaimer, the term of this patent is extended or adjusted under 35 U.S.C. 154(b) by 0 days.

(21) Appl. No.: 16/885,513

(22) Filed: May 28, 2020

(65) Prior Publication Data

US 2020/0356255 A1  Nov. 12, 2020

Related U.S. Application Data

(63) Continuation of application No. PCT/CN2017/113330, filed on Nov. 28, 2017.

(51) Int. Cl.
*G06F 3/04883* (2022.01)
*A61B 5/00* (2006.01)
(Continued)

(52) U.S. Cl.
CPC ........ *G06F 3/04883* (2013.01); *A61B 5/7435* (2013.01); *A61B 5/7445* (2013.01);
(Continued)

(58) Field of Classification Search
CPC .............. G06F 3/0488; G06F 3/04883; G06F 3/04845; G06F 1/1647; G06F 1/165; G06F 1/1654; G06F 2203/04806; A61B 5/7435
(Continued)

(56) References Cited

U.S. PATENT DOCUMENTS

| | | | |
|---|---|---|---|
| 2011/0118561 A1* | 5/2011 | Tari | A61B 5/7445 600/301 |
| 2011/0227739 A1* | 9/2011 | Gilham | G16H 40/63 345/545 |

(Continued)

FOREIGN PATENT DOCUMENTS

| CN | 101577108 A | * 11/2009 |
|---|---|---|
| CN | 101727305 A | 6/2010 |

(Continued)

OTHER PUBLICATIONS

International Search Report issued in corresponding International Application No. PCT/CN2017/113330, dated Aug. 20, 2018, 6 pages.

(Continued)

*Primary Examiner* — Reza Nabi
*Assistant Examiner* — Hwei-Min Lu
(74) *Attorney, Agent, or Firm* — Bayes PLLC (57) ABSTRACT

An monitor includes a host and a first display communicatively connected to the host. In a display screen switching method for the monitor, it is detected that a second display is connected, the second display is provided independently of the monitor. It is detected that a display screen switching instruction is received and a display file corresponding to configuration parameters of the second display is read, the display file includes one or more physiological parameters to be displayed, an interface layout and interface elements.

(Continued)

Data of the one or more physiological parameters are acquired according to the display file and generating frame data for representing pixel values of pixels on a display interface. The frame data are output to the second display to display data of the one or more physiological parameters.

20 Claims, 7 Drawing Sheets

(51) Int. Cl.
  *G06F 1/16* (2006.01)
  *G06F 3/04845* (2022.01)
(52) U.S. Cl.
  CPC ............ *G06F 1/165* (2013.01); *G06F 1/1654* (2013.01); *G06F 3/04845* (2013.01); *G06F 2203/04806* (2013.01)
(58) Field of Classification Search
  USPC ........................................................ 715/863
  See application file for complete search history.

(56) References Cited

U.S. PATENT DOCUMENTS

| | | | | |
|---|---|---|---|---|
| 2012/0081302 A1* | 4/2012 | Gimpl | ................... | G06F 3/0488 345/1.3 |
| 2013/0080931 A1* | 3/2013 | Sirpal | ................... | H05K 13/046 715/761 |
| 2013/0162502 A1* | 6/2013 | Lee | ................... | H04N 21/4363 345/1.2 |
| 2014/0194700 A1* | 7/2014 | Ikeya | ................... | A61B 5/742 600/300 |
| 2014/0203937 A1* | 7/2014 | Gilham | ................... | G16H 40/63 340/573.1 |
| 2014/0351738 A1 | 11/2014 | Kokovidis et al. | | |
| 2015/0302539 A1* | 10/2015 | Mazar | ................... | G08B 21/02 705/3 |
| 2018/0247712 A1* | 8/2018 | Muhsin | ................... | G16H 40/63 |
| 2019/0117070 A1* | 4/2019 | Muhsin | ................ | A61B 5/7425 |

FOREIGN PATENT DOCUMENTS

| | | | | | |
|---|---|---|---|---|---|
| CN | 101751864 A | | 6/2010 | | |
| CN | 102423256 A | * | 4/2012 | | |
| CN | 103282859 A | | 9/2013 | | |
| CN | 103908230 A | | 7/2014 | | |
| CN | 103941968 A | | 7/2014 | | |
| CN | 104545987 A | | 4/2015 | | |
| CN | 104750406 A | | 7/2015 | | |
| CN | 104750407 A | * | 7/2015 | ........... | G06F 19/321 |
| CN | 105703955 A | | 6/2016 | | |
| CN | 105912287 A | | 8/2016 | | |
| CN | 105930123 A | | 9/2016 | | |
| WO | 2009002744 A1 | | 12/2008 | | |

OTHER PUBLICATIONS

First Office Action issued in Chinese application No. 201780097185.4, dated Sep. 7, 2022, 19 pages.

* cited by examiner

MONITOR AND DISPLAY SCREEN SWITCHING METHOD THEREFOR

CROSS-REFERENCE TO RELATED APPLICATIONS

This application is a bypass continuation of PCT Application No. PCT/CN2017/113330, filed Nov. 28, 2017, which is incorporated herein by reference.

TECHNICAL FIELD

The disclosure relates to medical equipment, in particular to a monitor and a display screen switching method therefor.

BACKGROUND

A medical monitor is used to measure and process physiological parameters of a patient, detect change trends, and display waveforms or values of physiological parameters on a display screen for medical personnel to check at any time. In addition, the monitor can also compare the patient's physiological parameters with preset threshold values, giving an alarm in case of emergencies to inform the medical personnel, and providing a basis for physicians to deal with the emergencies and carry out treatment. Therefore, the monitor must continuously monitor the patient's physiological parameters. Even if the patient is being transferred from one ward or department to another, there's also an accompanying monitor provided beside the patient's transfer bed usually.

In order to facilitate transfer, medical personnel usually choose monitors with smaller screen sizes as the transfer monitors, but displays with small screens often have insufficient display area and resolution and cannot display more contents and clearer images. Therefore, after the patient is transferred to the destination, for the convenience of viewing, it is necessary to replace the transfer monitor with a large bedside display screen to meet requirements of monitoring.

One current technical solution for the display of bedside expansion screens adding separate hardware and software to realize a large independent bedside screen display. The problem is that the overall system is complicated and expensive. Another solution is directly mirroring the display image of a transfer monitor onto a large external screen for enlarged display. However, the display effect of the enlarged direct mirror image is not good as the screen size of the transfer monitor differs greatly from that of the external screen.

SUMMARY

The disclosure mainly provides a monitor and a display screen switching method therefor in order to facilitate display screen switching by a user.

In one embodiment, a display screen switching method for a monitor comprises a host and a first display communicatively connected to the host, the method comprising:

the monitor detecting whether a second display is connected, the second display being provided independently of the monitor;

once connection to the second display is detected, detecting whether a display screen switching instruction is received;

if the display screen switching instruction is received, reading a corresponding display file according to configuration parameters of the second display, the display file comprising physiological parameters to be displayed, interface layout and interface elements;

acquiring data of the physiological parameters according to the display file and generating frame data, the frame data being used for representing pixel values of pixels on a display interface; and outputting the frame data to the second display to display physiological data.

In one embodiment, a display screen switching method for a monitor comprises a host and a first display communicatively connected to the host, the method comprising:

the monitor detecting whether a second display is connected;

once connection to the second display is detected, reading a corresponding display file according to configuration parameters of the second display, the display file comprising physiological parameters to be displayed, interface layout and interface elements;

acquiring data of the physiological parameters according to the display file and generating frame data, the frame data being used for representing pixel values of pixels on a display interface; and outputting the frame data to the second display to display physiological data.

In one embodiment, a display screen switching method for a monitor comprises a host for communicative connection to a first display and a second display, the method comprising:

the monitor detecting and receiving a display screen switching instruction;

identifying a display indicated by the display screen switching instruction as a switching target;

reading a corresponding display file according to configuration parameters of the display identified as the switching target, the display file comprising physiological parameters to be displayed, interface layout and interface elements;

acquiring data of the physiological parameters according to the display file and generating frame data, the frame data being used for representing pixel values of pixels on a display interface; and outputting the frame data to the display identified as the switching target to display physiological data.

In one embodiment, a computer-readable storage medium comprises a program that can be executed by a controller to implement the above method.

In one embodiment, a monitor, comprises:

a first display;

a first interface circuit, one end of which is connected to a host and the other end of which is connected to the first display;

a second interface circuit comprising a pluggable interface, the second interface circuit having one end connected to the host and the other end for connection to a second display, and outputting a first indication signal when being connected to the second display and a second indication signal when being disconnected from the second display; and the host comprising a controller, a memory, and at least one parameter module for receiving physiological parameters sensed by a sensor and processing the physiological parameters; the memory being used for storing display files corresponding to configuration parameters of the displays, the display files comprising physiological parameters to be displayed, interface layout and interface elements; and the controller being used for determining whether the second display is connected according to the indication signals output from the second interface circuit, detecting whether a display screen switching instruction is received once connection to the second display is detected, reading the corresponding display file from the memory according to configuration parameters of the second display if the display screen switching instruction is received, acquiring data of the physiological parameters from the parameter module according to the display file and generating frame data for representing pixel values of pixels on a display interface, and outputting the frame data to the second display to display physiological data.

In one embodiment, a monitor, comprises:

a first display;

a first interface circuit, one end of which is connected to a host and the other end of which is connected to the first display;

a second interface circuit comprising a pluggable interface, the second interface circuit having one end connected to the host and the other end for connection to a second display, and outputting a first indication signal when being connected to the second display and a second indication signal when being disconnected from the second display; and the host comprising a controller, a memory, and at least one parameter module for receiving physiological parameters sensed by a sensor and processing the physiological parameters; the memory being used for storing display files corresponding to configuration parameters of the displays, the display files comprising physiological parameters to be displayed, interface layout and interface elements; and the controller being used for determining whether the second display is connected according to the indication signals output from the second interface circuit, reading the corresponding display file from the memory according to the configuration parameters of the second display once connection to the second display is detected, acquiring data of the physiological parameters from the parameter module according to the display file and generating frame data for representing pixel values of pixels on a display interface, and outputting the frame data to the second display to display physiological data.

In one embodiment, a monitor comprises:

a first interface circuit, one end of which is connected to a host and the other end of which is connected to the first display;

a second interface circuit, one end of which is connected to the host and the other end of which is connected to a second display;

the host comprising a controller, a memory, and at least one parameter module for receiving physiological parameters sensed by a sensor and processing the physiological parameters; the memory being used for storing display files corresponding to configuration parameters of the displays, the display files comprising physiological parameters to be displayed, interface layout and interface elements; and the controller being used for detecting and receiving a display screen switching instruction, identifying a display indicated by the display screen switching instruction as a switching target, reading the corresponding display file from the memory according to the configuration parameters of the display identified as the switching target, acquiring data of the physiological parameters from the parameter module according to the display file and generating frame data for representing pixel values of pixels on a display interface, and outputting the frame data to the display identified as the switching target to display physiological data.

In one embodiment, a display screen switching method for a monitor comprises:

the monitor detecting whether a second display is connected, the second display being provided independently of the monitor;

once the connection to the second display is detected, outputting and displaying physiological data received by the monitor by the way of:

detecting a first display screen switching instruction input on a first display provided on the monitor;

if the first display screen switching instruction is detected, reading a corresponding first display file according to configuration parameters of the first display, the first display file comprising physiological parameters to be displayed, interface layout and interface elements, acquiring data of the physiological parameters according to the first display file and generating first frame data, the first frame data being used for representing pixel values of pixels on a display interface corresponding to the configuration parameters of the first display, and outputting the first frame data to the first display for display;

detecting a second display screen switching instruction input on the first display and/or the second display; and if the second display screen switching instruction is detected, or the second display screen switching instruction is not detected within a specified time period, reading a corresponding second display file according to configuration parameters of the second display, the second display file comprising physiological parameters to be displayed, interface layout and interface elements, acquiring data of the physiological parameters according to the second display file and generating second frame data, the second frame data being used for representing pixel values of pixels on a display interface corresponding to the configuration parameters of the second display, and outputting the second frame data to the second display for display.

In the embodiments of the disclosure, the transfer monitor is provided with a plurality of display modes. When display by the first display is required, a display mode I is switched on by an instruction, and when display by the second display is required, a display mode II is switched on by an instruction, so that each display can display adapted physiological data.

DETAILED DESCRIPTION

The present disclosure will be further described in detail below through specific embodiments in conjunction with the accompanying drawings, where like elements in different embodiments are designated by associated like reference numerals. In the following embodiments, many details are described for the purpose of facilitating better understanding of the present application. However, it would be effortlessly appreciated by those skilled in the art that some features may be omitted or may be substituted by other elements, materials and methods in a different case. In certain cases, some operations relevant to the present application are not shown or described in the specification, so as to prevent the core part of the present application from being obscured by too much description. Moreover, for those skilled in the art, the detailed description of those relevant operations is not necessary, and those relevant operations can be thoroughly understood based on the description in the specification and the general technical knowledge in the art.

In addition, the characteristics, operations or features described in the specification can be combined in any appropriate manner to form various embodiments. Moreover, the order of steps or actions in the method description can also be changed or adjusted in a way that would have been obvious to those skilled in the art. Therefore, the orders in the specification and drawings are merely for the purpose of clear description of a certain embodiment and are not meant to be a necessary order unless otherwise stated that a certain order must be followed.

As used herein, serial numbers assigned to components, such as "first", "second", are only used to distinguish the described objects and do not have any sequential or technical meaning. The term "connect" and "connection" as used herein includes direct and indirect connection (coupling) unless otherwise specified.

Figure 1:
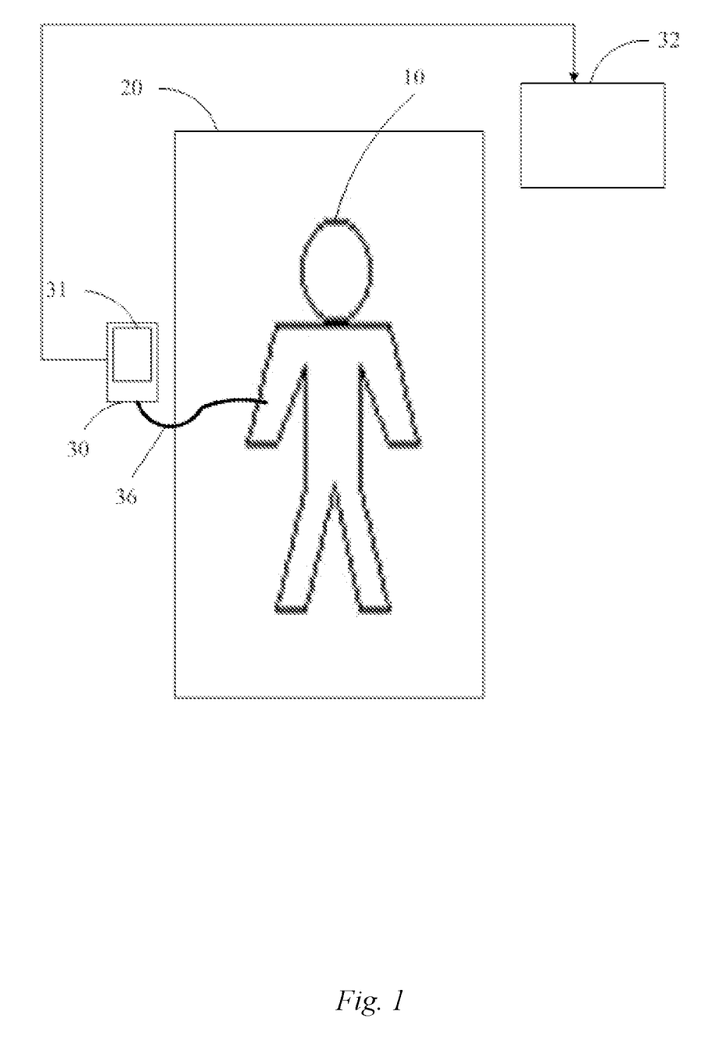
FIG. 1 is a schematic diagram of patient transfer.

Referring to FIG. 1, a patient 10 is equipped with a monitor 30 beside his/her transfer bed 20 during transfer. The monitor 30 detects physiological parameters of the patient 10 through a detection terminal 36. Normally, the monitor is a portable device with a small volume, so a first display 31 with a small screen size is provided along with it. After arriving at the destination, the monitor 30 will be placed on a docking station (not shown) for connecting to a power supply via the docking station and also for connecting to a second display 32 via the docking station. The second display 32 has a larger display screen.

The first display 31 and the second display 32 are quite different in screen size and resolution. The screen size of the second display 32 is larger than that of the first display 31. For example, the screen size of the first display 31 may be equivalent to that of a smart phone, while the screen of the second display 32 may be tens of times larger than that of the first display 31. In addition, the first display 31 is generally a portrait screen while the second display 32 is generally a landscape screen. These differences result in a poor display effect if an interface suitable for display on the first display 31 is directly mirrored onto the second display 32, and a problem of incomplete display if an interface suitable for display on the second display 32 is mirrored onto the first display 31.

In this embodiment, the transfer monitor is provided with various display modes, for example, a display mode I and a display mode II, wherein the display mode I is designed according to the screen length and width and resolution of the first display of the transfer monitor, and the display mode II is designed according to the screen length and width and resolution of the external second display. When the monitor detects no connection to the second display, the monitor remains processing data according to the display mode I, and the physiological data is displayed by the first display. When the monitor detects a connection to the second display, the monitor can switch to the display mode II automatically or according to a display screen switching instruction, such that the second display can display the adapted physiological data.

Figure 2:
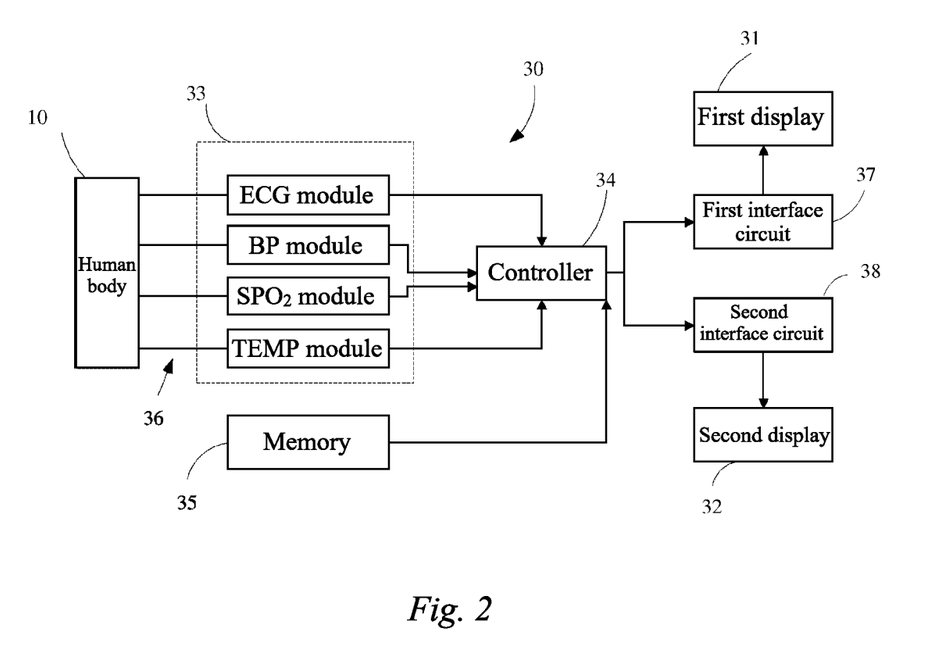
FIG. 2 is a schematic structural diagram of a monitor in an embodiment.

Referring to FIG. 2, the monitor 30 comprises a first display 31, a host, a first interface circuit 37 and a second interface circuit 38. The monitor 30 is further configured for signal connection to the second display 32 through the docking station.

In one of the embodiments, the first display 31 and the second display 32 may be liquid crystal displays optionally, and the screen size of the second display 32 is larger than that of the first display 31. The first display 31 may further comprise a touch screen, so that a user can issue a display screen switching instruction by touching the touch screen. In other embodiments, the first display 31 may further comprise a photographing device (e.g., a camera), such that a display screen switching instruction can be generated by photographing a gesture of a user with the photographing device.

In a specific embodiment, the first display 31 can directly use a touch display screen with a vertical screen refresh mode, a resolution of 720 P or more and a surface area of 195 square centimeters or less.

One end of the first interface circuit 37 is connected to the host, and the other end of the first interface circuit 37 is connected to the first display 31. When the format of frame data output from the host is consistent with the required format of frame data input to the first display 31, the first interface circuit 37, which may serve as a transmission line, for example, is used for signal transmission between the host and the first display 31. When the format of the frame data output from the host is inconsistent with the required format of the frame data input to the first display 31, the first interface circuit 37 is further used to convert the data in a first format output from the host into the data in a second format adapted to the first display. For example, data in RGB, LVDS, eDP and other formats are converted into data in an MIPI CSI format. The first interface circuit 37 may be implemented using a dedicated conversion chip or an FPGA chip. In some embodiments, the first interface circuit 37 may use a fixed interface to fixedly connect the first display 31 to the host for integration. The first interface circuit 37 may also include a pluggable interface such that when the first display 31 is plugged into the interface, the first display 31 is connected to the host, and when the first display 31 is unplugged from the interface, the first display 31 is disconnected from the host. In some embodiments, the type of the display interface of the first interface circuit 37 includes at least: one of an MIPI CSI and an MIPI DSI display interface.

In some embodiments, the first display above may be a local display of the monitor, the second display may be an external display independent of or separate from the monitor, and the second display and the monitor may be connected via a connection line for information/data transmission.

One end of the second interface circuit 38 is connected to the host, and the other end of the second interface circuit 38 is for connection to the second display 32. When the format of frame data output from the host is consistent with the required format of frame data input to the second display 32, the second display 32 is used for signal transmission between the host and the second display 32, for example, which may be a transmission line. When the format of the frame data output from the host is inconsistent with the required format of the frame data input to the second display 32, the second display 32 is further used for converting the data in the first format output from the host into the data in a third format adapted to the second display. For example, data in RGB, LVDS, eDP and other formats are converted into data in VGA, DVI, HDMI, DP and other formats. The second interface circuit 38 may also be implemented using a dedicated conversion chip or an FPGA chip. In practical application, the second interface circuit 38 comprises a pluggable interface, so that when the second display 32 is plugged into the interface, the second display 32 is connected to the host, and at this time, the second interface circuit 38 outputs a first indication signal, such as a high/low level signal, indicating that the monitor is connected to the second display; and when the second display 32 is unplugged from the interface, the second display 32 is disconnected from the host, and at this time, the second interface circuit 38 outputs a second indication signal, such as a low/high signal, indicating that the monitor is disconnected from the second display. In some embodiments, the type of the display interface of the first interface circuit 37 includes at least: one of an MIPI CSI, an MIPI DSI display interface, an RGB display interface, an LVDS display interface and an eDP display interface.

In addition, in some embodiments, the first interface circuit or the second interface circuit further comprises a connection detection circuit for detecting the electric connection state of the second interface circuit or the first interface circuit with the second display or the first display, respectively. For example, whether the second interface circuit is connected to the second display can be determined by the electric connection detection via the connection detection circuit when the second interface circuit is connected to the second display, and thus, it can be determined that whether the monitor connected to the second interface circuit detects the connection to the second display. Alternatively, for example, whether the first interface circuit is connected to the first display can be determined by the electric connection detection via the connection detection circuit when the first interface circuit is connected to the first display, and thus, it can be determined that whether the monitor connected to the first interface circuit detects the connection to the first display.

The host comprises a controller 34, a memory 35 and at least one parameter module 33. The parameter module 33 is used for receiving physiological parameters sensed by the detection terminal 36 and processing the physiological parameters, and can be a plug-in multi-parameter module, including such as an ECG module, a BP module, an SPO2 module and a TEMP module. The ECG module is used to acquire electrocardio signals of the patient 10 through leads and obtain electrocardiograms and one or more bands of interest such as P waves, T waves, QRS waves, ST waves, etc. through processing. The BP module is used to collect the pulse wave of the patient 10 through a sensor and obtain various blood pressure values or blood pressure change waveforms through calculation. The SPO2 module is used to measure an amount of light absorption by the patient 10 through a sensor and obtain the blood oxygen saturation through calculation. The TEMP module is used to measure the body temperature of the patient 10 through a thermometer. Those skilled in the art will understand that the parameter module 33 may also include more or fewer physiological parameter measurement modules.

The memory 35 is used for storing various data, files and programs. In this embodiment, the memory 35 stores display files, and there may be multiple display files corresponding to the configuration parameters of the displays, respectively, and different display configuration parameters correspond to different display files. Each display file comprises contents corresponding to the display configuration parameters, including physiological parameters to be displayed, interface layout and interface elements on the display. For a multi-parameter monitor, many physiological parameters can be monitored, such as ECG, HR, SPO2, NIBP, RESP and TEMP. When the monitor uses a large screen for display, more data and/or waveforms of physiological parameters can be displayed per screen, and also, many function keys can be designed on the display interface. However, when the monitor uses a small screen for display, in order to achieve a good display effect, only data and/or waveforms of a few physiological parameters can be displayed per screen, for example, only the data and/or waveforms of the most critical physiological parameters are displayed, and the others are displayed by scrolling, and moreover, there is no space on the display interface for the design of many function keys. Therefore, displays with different display configurations display different physiological parameters per screen. Different physiological parameters require different display methods. For example, some physiological parameters are displayed by waveforms, some by numerical values, and some by both. Therefore, the interface layout and interface elements of displays with different display configurations may also be different. For example, the interface elements may include icons, windows, menus, dialog boxes, scroll bars, graphics, etc. The interface layout specifies the location, size, etc. of the interface elements.

The controller 34 is in signal connection to the memory 35 and the parameter module 33, respectively, and is in signal connection to the first display 31 and the second display 32 through the first interface circuit 37 and the second interface circuit 38, respectively. The controller 34 is used for determining whether the second display is connected according to the indication signals output from the second interface circuit, detecting whether a display screen switching instruction is received once connection to the second display is detected, reading the corresponding display file from the memory according to configuration parameters of the second display if the display screen switching instruction is received, acquiring data of the physiological parameters from the parameter module according to the display file and generating frame data for representing pixel values of pixels on a display interface, and outputting the frame data to the second display to display physiological data.

Figure 3:
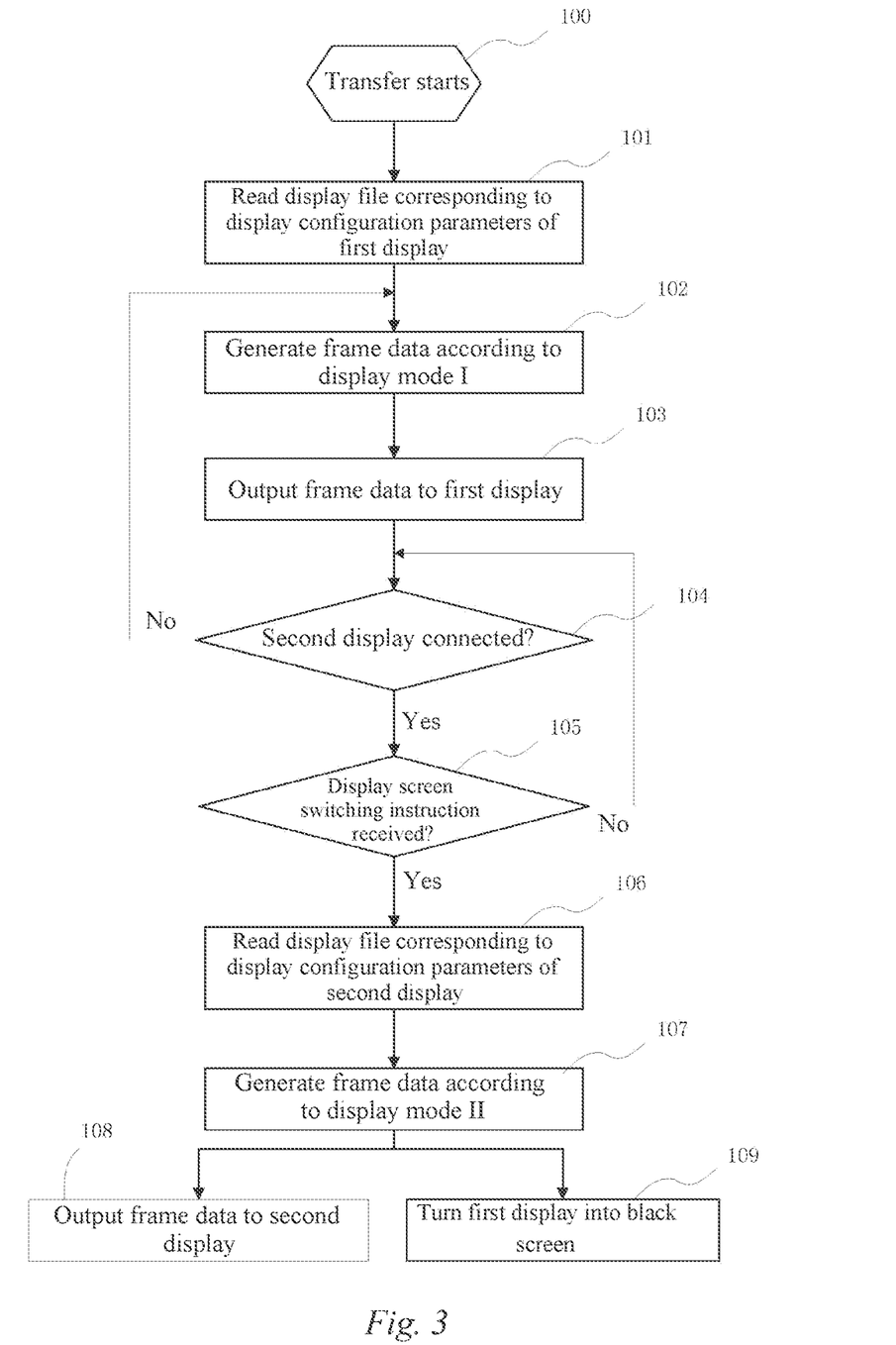
FIG. 3 is a flowchart of a monitor switching from a display mode I to a display mode II in one embodiment.
Figure 5:
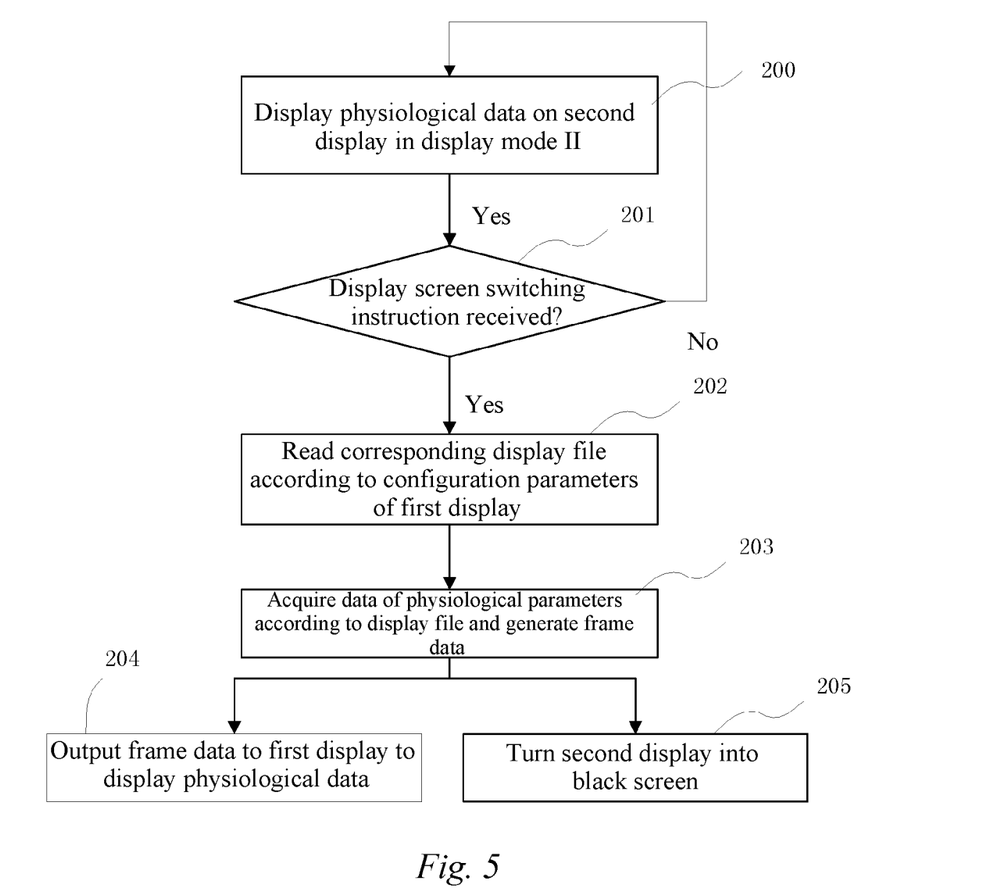
FIG. 5 is a flowchart of a monitor switching from the display mode II to the display mode I in one embodiment.

The controller 34 controls the workflow of switching the display modes as shown in FIGS. 3 and 5. FIG. 3 shows the workflow of switching from the display mode I to the display mode II, comprising the following steps:

Step 100: transfer starts. At this time, the monitor is configured with the first display. During the transfer process, the physiological parameters of the patient are continuously and uninterruptedly collected, and the physiological parameters of the patient can be displayed on the first display in the display mode I. The displayed contents include the values of the physiological parameters, real-time waveform data of the physiological parameters, etc.

Step 101: read the display file corresponding to display configuration parameters of the first display. Firstly, the controller obtains the display configuration parameters of the first display, and then reads the display file corresponding to the display configuration of the first display from the memory. The display file specifies which physiological parameters to be displayed on the first display per screen, the layout of the display interface, and which interface elements to be displayed on the display interface. The display interface generated according to the display file is referred to as the display mode I.

Step 102: generate frame data according to the display mode I. For example, data of the physiological parameters can be obtained according to the display file obtained in step 101 and frame data can be generated. The frame data is used to represent pixel values of pixels on the display interface. The controller acquires the data of the physiological parameters from the parameter module according to the display mode I, and generates the frame data through conversion for representing the pixel values of the pixels on the display interface. The frame data specifies the pixel value of each pixel point in each frame image, and the pixel value may be a gray value or an RGB value. Frame data is output according to the standard of the RGB, LVDS or eDP internal display interface. When the first display is a display using a vertical screen refresh mode, the display interface formed by the frame data output from the controller is of vertical refresh, and when the first display is a landscape screen display, the display interface formed by the frame data output from the controller is of horizontal refresh.

Figure 4A:
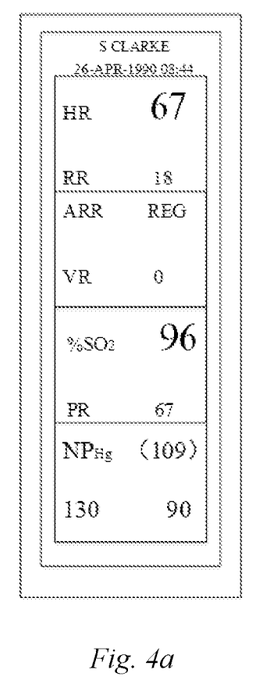
FIG. 4a and FIG. 4b are schematic diagrams of interfaces in the display mode I and the display mode II, respectively.

Step 103: output the frame data to the first display. When the format of the frame data output from the controller is inconsistent with the required format of the frame data input to the first display, the frame data in RGB, LVDS, eDP and other formats output from the controller need to be converted into the frame data in a format consistent with the input format of the first display through conversion by the first interface circuit 37 before outputting the frame data to the first display. The first display receives the frame data and displays the physiological data according to the display mode I. For example, in one embodiment, the display interface in the display mode I is a vertically refreshed display interface, as shown in FIG. 4a.

Step 104: detect whether the second display is connected. If not, the workflow returns to step 102. When the patient has been transferred to the destination, medical personnel will plug the monitor into the docking station, and the interface of the docking station is connected to the second display, so the monitor will be connected to the second display through the docking station. Once connection to the second display is detected, the workflow proceeds to step 105.

Step 105: detect whether a display screen switching instruction is received, and if not, cyclically detect whether a display screen switching instruction is received, and perform step 106 when the display screen switching instruction is received. In this embodiment, the display screen switching instruction is generated by a gesture of a user touching the touch screen, and the gesture may be a sliding, tapping, zooming or dragging operation. The sliding can be performed by a single finger, two fingers, three fingers or four fingers, and the sliding direction can also be upward, downward, leftward or rightward. Tapping can be a single-tap or a double-tap, etc. Under normal circumstances, the first display is arranged at the bedside, and the display screen switching command can be input from the first display. Of course, the second display is arranged at a farther position relative to the bed, and the display screen switching instruction can also be input from the second display. In the design of the gesture of the display screen switching instruction, a gesture of sliding from the bottom left to the top right can be adopted, that is, when the controller detects that a user slides from the bottom left to the top right on the touch screen, the user is deemed to input a display screen switching instruction. The action triggering the display mode switching operation is not necessarily a fixed action, but may also be a user-defined action. In some embodiments, when the first display comprises a photographing device, the display screen switching instruction can also be generated by a gesture photographed by the photographing device, wherein the gesture may be sliding, zooming or a static gesture of fingers made in front of the photographing device. In other embodiments, the display screen switching instruction can also be generated by a user operating a physical operation key arranged on the monitor, and the operation key can be a button, a knob, a toggle switch or a soft key designed on the display screen.

Step 106: read the display file corresponding to configuration parameters of the second display. Firstly, the controller obtains the display configuration parameters of the second display, which can be stored in the memory in advance, or otherwise can be transmitted to the controller by the second display when the second display is connected. Then the controller reads the display file corresponding to the display configuration of the second display from the memory. The display file specifies which physiological parameters to be displayed on the second display per screen, the layout of the display interface, and which interface elements to be displayed on the display interface. The display interface generated according to the display file is referred to as the display mode II.

Step 107: generate frame data according to the display mode II. The data of the physiological parameters are acquired from the parameter module according to the display mode II, and the frame data for representing the pixel values of the pixels on the display interface are generated through conversion.

Figure 4B:
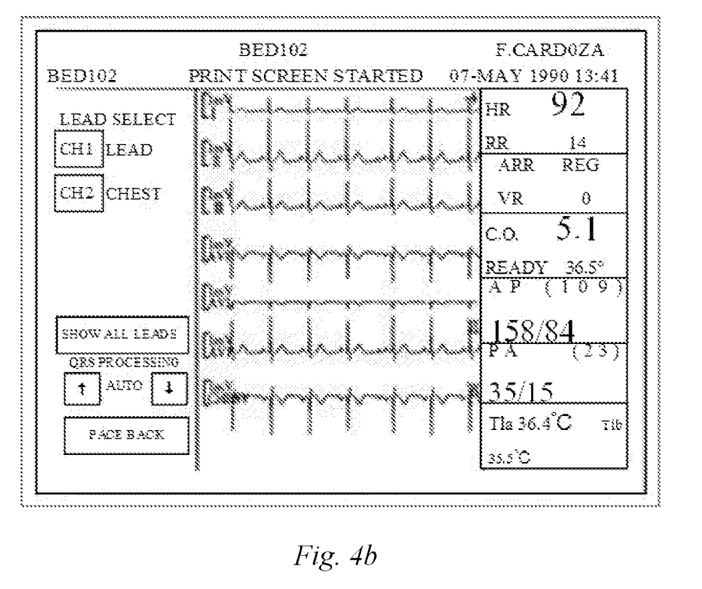

Step 108: output the frame data to the second display. When the format of the frame data output from the controller is inconsistent with the required format of the frame data input to the second display, the frame data in RGB, LVDS, eDP and other formats output from the controller need to be converted into the frame data in a format consistent with the input format of the second display through conversion by the second interface circuit 38 before outputting the frame data to the second display. The second display receives the frame data and displays the physiological data in the display mode II to achieve a better large screen display effect. For example, the display interface of the display mode II is a landscape interface, as shown in FIG. 4b.

Moreover, one of the embodiments may further comprise a step 109 of turning the first display into a black screen. The controller can turn the first display into a black screen by turning off the power supply or backlight of the first display. For example, when the controller detects that a user issues a display screen switching instruction by a gesture of touching the touch screen, the controller immediately turns off the backlight of the first display, and at this time, even if the controller also outputs frame data to the first display at the same time, the user cannot see the display content on the first display since the first display is black.

In step 109, turning off the power supply or backlight of the first display is preferably performed at the same time as the starting display of the second display, thus giving the user the illusion that the display content is thrown from the first display to the second display by his/her own gesture, and providing the user with a sense of engagement while performing appropriate display according to the displays. Of course, in other embodiments, those skilled in the art can understand that step 109 can also be omitted, in which case the first display and the second display will simultaneously display the physiological data in the mode II.

Of course, in other embodiments, frame data are generated from the physiological data collected by the monitor according to the display file corresponding to the configuration parameters of the first display, such that the frame data are simultaneously output on the first display to display the physiological data, thus realizing the synchronous display of the physiological parameters by both the first display and the second display.

FIG. 5 shows the workflow of switching from the display mode II to the display mode I, comprising the following steps:

Step 200: display physiological data on the second display in the display mode II. In the case where the second display is displaying the physiological data, the data of the physiological parameters are acquired from the parameter module according to the display mode II, the frame data for representing the pixel values of the pixels on the display interface are generated through conversion, and the frame data is output to the second display, such that the second display displays the physiological data in the display mode II.

Step 201: detect whether a display screen switching instruction is received, and proceed to step 202 when the display screen switching instruction is received.

Step 202: read a corresponding display file according to configuration parameters of the first display.

Step 203: acquire data of physiological parameters according to the display file and generate frame data.

Step 204: output the frame data to the first display to display the physiological data, which can be displayed in the form of waveform charts, trend charts, texts or numbers.

Step 205: turn the second display into a black screen. When the first display starts displaying, the power supply or backlight of the second display is turned off to make the second display black.

In step 201, the way for generating a display screen switching instruction may be the same as that for generating an instruction when switching from the display mode I to the display mode II, i.e., the instruction may be generated by the same operation. For example, it can be the same gesture. Of course, the display screen switching instruction in step 201 may otherwise differ from that when switching from the display mode I to the display mode II. For example, the instructions are generated by opposite operations. For example, a slide from the bottom left to the top right generates an instruction to switch from the display mode I to the display mode II, and a slide from the top right to the bottom left generates an instruction to switch from the display mode II to the display mode I along with turning the second display screen into a black screen at the same time, giving the user an illusion that the display content is pulled back from the second display to the first display by his/her own gesture.

In this embodiment, the instruction to switch between the display mode I and the display mode II is generated by an operation on the first display. Since the first display is usually arranged at the bedside, this design facilitates the operation by the user.

Figure 6:
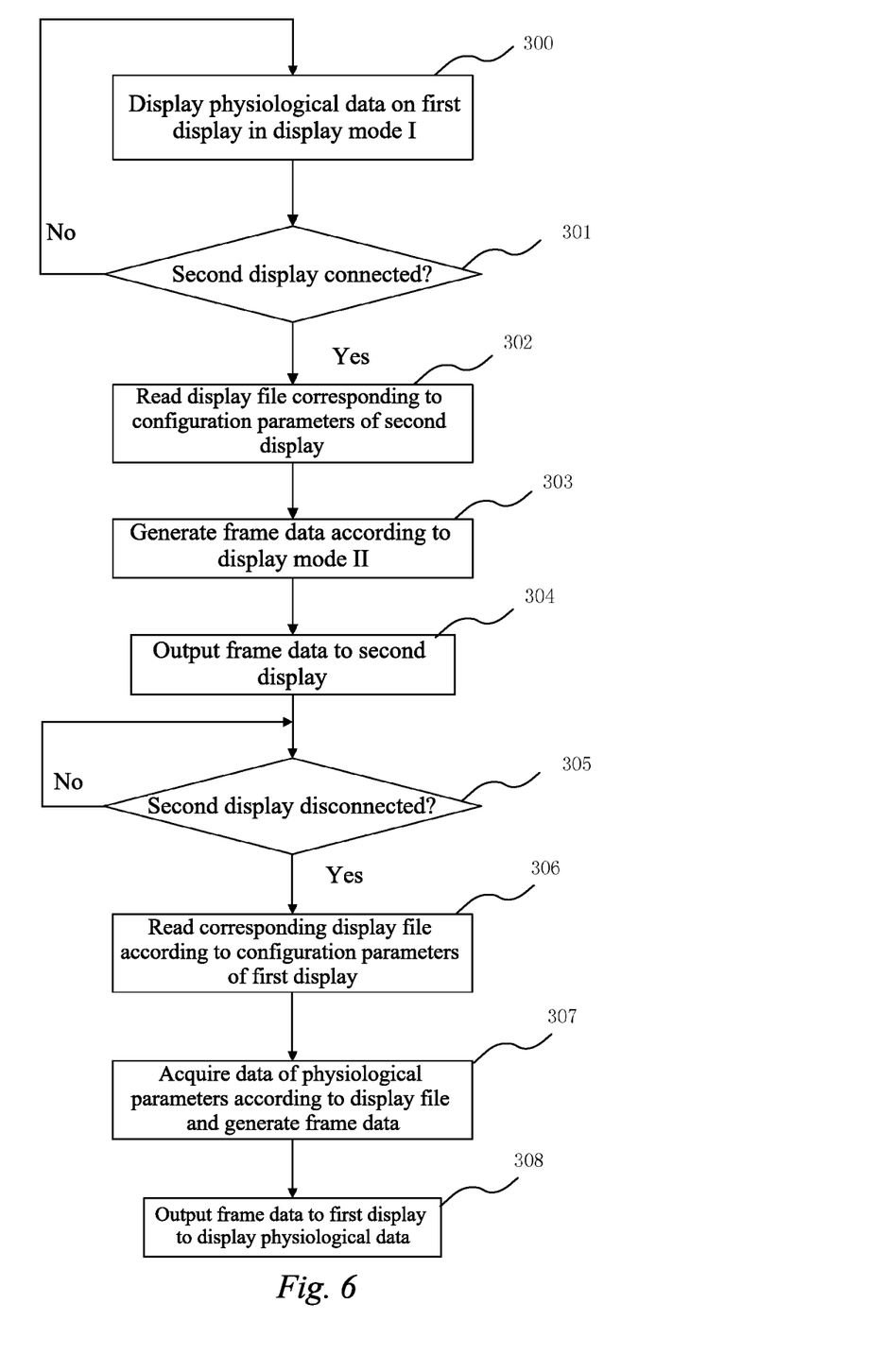
FIG. 6 is a flowchart of a monitor automatically switching display modes in one embodiment.

In other embodiments, the second display may also comprise a touch screen, and the display screen switching instruction may also be generated by a gesture of a user touching the touch screen of the second display. Alternatively, the second display may also comprise a photographing device, such that the display screen switching instruction can also be generated by a gesture photographed by the photographing device In this embodiment, when switching between the display mode I and the display mode II, the switching need not be triggered by the display screen switching instruction. Instead, the display mode I and the display mode II are automatically switched according to the condition of the connected display. As shown in FIG. 6, the workflow of this embodiment comprises the following steps. The detailed operations of some steps are the same as the corresponding steps in Embodiment 1, and will not be repeated here.

Step 300: display physiological data on the first display in the display mode I.

Step 301: the monitor detects whether the second display is connected, and proceeds to step 302 once connection to the second display is detected.

Step 302: read a corresponding display file according to configuration parameters of the second display.

Step 303: acquire data of physiological parameters according to the display file and generate frame data.

Step 304: turn the first display into a black screen while outputting the frame data to the second display to display the physiological data.

Step 305: the monitor detects whether the second display is disconnected. Once disconnection from the second display is detected, the workflow proceeds to step 306.

Step 306: read a corresponding display file according to configuration parameters of the first display.

Step 307: acquire data of physiological parameters according to the display file and generate frame data.

Step 308: turn the second display into a black screen while outputting the frame data to the first display to display the physiological data.

Figure 7:
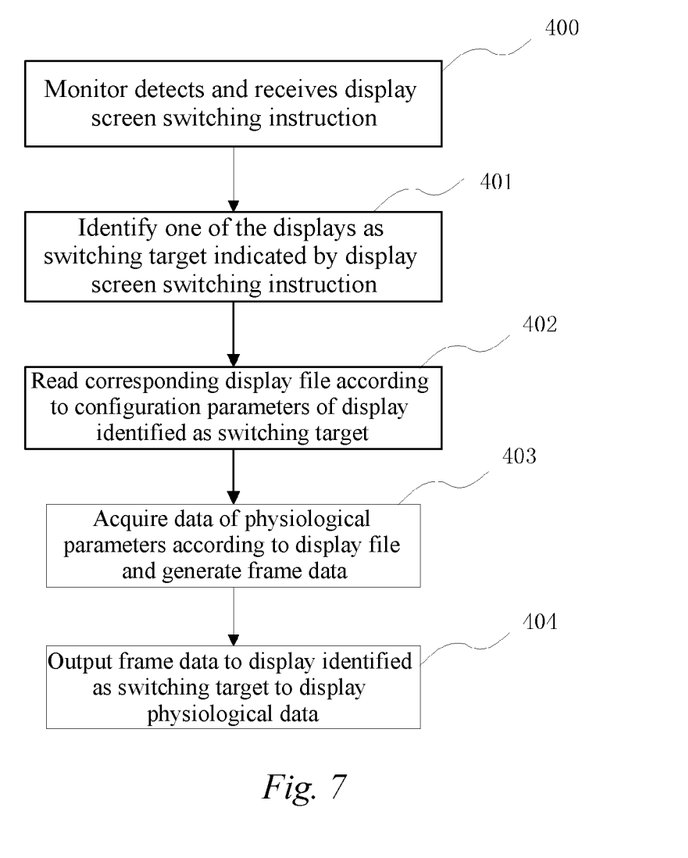
FIG. 7 is a flowchart of a monitor switching display modes in another embodiment.

In this embodiment, the user indicates the target display to which he/she wants to switch through a display screen switching instruction, wherein the instruction to switch from the display mode I to the display mode II and the instruction to switch from the display mode II to the display mode I are generated in different ways, the generated instructions are also different, and the displays identified as the switching targets by different instructions are also different. As shown in FIG. 7, the processing workflow of this embodiment comprises the following steps:

Step 400: the monitor detects and receives a display screen switching instruction.

Step 401: identify a display indicated by the display screen switching instruction as a switching target. Taking the display screen switching instruction generated by a sliding gesture as an example, when the sliding gesture is a slide from the bottom left to the top right, the controller considers the second display as the switching target display indicated by the display screen switching instruction; and when the sliding gesture is a slide from the top right to the bottom left, the controller considers the first display as the switching target display indicated by the display screen switching instruction. Alternatively, a gesture operating on the first display regards the display screen switching instruction as pointing to the first display and takes the first display as the switching target display, whereas the gesture operating on the second display regards the display screen switching instruction as pointing to the second display and takes the second display as the switching target display.

Step 402: read the corresponding display file according to the configuration parameters of the display identified as the switching target.

Step 403: acquire data of physiological parameters according to the display file and generate frame data.

Step 404: output the frame data to the display identified as the switching target to display physiological data.

In this embodiment, the user indicates the target display to which he/she wants to switch through a display screen switching instruction, and can switch between the display mode I and the display mode II. The switching method in this embodiment comprises the steps of:

reading a corresponding first display file according to configuration parameters of the first display, the first display file comprising physiological parameters to be displayed, interface layout and interface elements, acquiring data of the physiological parameters according to the first display file and generating first frame data, the first frame data being used for representing pixel values of pixels on a display interface corresponding to the configuration parameters of the first display; and outputting the first frame data to the first display and the second display for display.

The first display file mentioned in this embodiment can be used to generate frame data for displaying physiological data in the display mode I. Similarly, the controller can also read a corresponding second display file according to configuration parameters of the second display, the second display file comprising physiological parameters to be displayed, interface layout and interface elements, acquire data of the physiological parameters according to the second display file and generate second frame data, the second frame data being used for representing pixel values of pixels on a display interface corresponding to the configuration parameters of the second display, and output the second frame data to the second display for display. The second display file here can be used to generate frame data for displaying physiological data in the display mode II.

In one of the embodiments, the monitor receives an activation command that is externally input, for example, the activation command may be a gesture input of touching the touch screen on the first display, or based on the input of a physical operation key on the monitor or the second display. The gesture input includes and is not limited to a double-tap on the display screen, a sliding gesture, etc.; and the physical operation key includes and is not limited to a power key, a setting key, etc.

For example, in one of the embodiments, the switching method above can use the following steps:

the monitor detecting whether a second display is connected, the second display being provided independently of the monitor; and once the connection to the second display is detected, outputting and displaying physiological data received by the monitor by:

step A1: detecting a first display screen switching instruction input on first display provided on the monitor;

step A2: if the first display screen switching instruction is detected, reading a corresponding first display file according to configuration parameters of the first display, the first display file comprising physiological parameters to be displayed, interface layout and interface elements, acquiring data of the physiological parameters according to the first display file and generating first frame data, the first frame data being used for representing pixel values of pixels on a display interface corresponding to the configuration parameters of the first display, and outputting the first frame data to the first display for display;

step A3: detecting a second display screen switching instruction input on the first display and/or the second display, wherein the second display is provided independently of the monitor; and step A4: if the second display screen switching instruction is detected, or the second display screen switching instruction is not detected within a specified time period, reading a corresponding second display file according to configuration parameters of the second display, the second display file comprising physiological parameters to be displayed, interface layout and interface elements, acquiring data of the physiological parameters according to the second display file and generating second frame data, the second frame data being used for representing pixel values of pixels on a display interface corresponding to the configuration parameters of the second display, and outputting the second frame data to the second display for display.

Steps A1, A2, A3, and A4 may be performed by the same controller or by different controllers. For example, the operation for step A1 is performed by a controller connected to the first display, and the detection for step A3 is performed by a controller connected to the second display that has a gesture tracking detection function.

The first display screen switching instruction and the second display screen switching instruction in this embodiment may be the same command or different commands. For example, the first display screen switching instruction and/or the second display screen switching instruction may be a gesture input of touching the touch screen on the first display, or based on an input of a physical operation key on the monitor or the second display. The above description with regard to the display screen switching instruction can be referred to for details of the first display screen switching instruction and the second display screen switching instruction.

For example, in one of the embodiments, the process of detecting a second display screen switching instruction input on the first display and/or the second display in the above method comprises one of the following:

detecting whether there is an input of a second display screen switching instruction on the first display;

detecting whether there is a second display screen switching instruction on the second display; and detecting whether there is no input of a second display screen switching instruction on the first display or the second display within a specified time period.

In one of the embodiments, the detection of the first display screen switching instruction input on the first display or the detection of the second display screen switching instruction input on the first display and/or the second display can comprise the step of:

detecting whether there are two consecutive inputs at a predetermined frequency at the same position of the display interface of the first display or the second display, if so, indicating that the display screen switching instruction is detected.

In one of the embodiments, the detection of the first display screen switching instruction input on the first display or the detection of the second display screen switching instruction input on the first display and/or the second display can comprise the step of:

detecting whether a gesture input on the display interface of the first display or the second display has a predetermined acoustic characteristic, and if so, indicating that the display screen switching instruction is detected. For example, it is detected whether there is a double-tap command on the display interface of the first display or the second display, and if so, it is indicated that a display screen switching instruction is detected. Those skilled in the art would have understood that all or some of the functions of the various methods in the above embodiments may be implemented by means of hardware or by means of a computer program. When all or some of the functions in the above embodiments are implemented by means of a computer program, the program may be stored in a computer-readable storage medium, and the storage medium may include: a read-only memory, a random access memory, a magnetic disk, an optical disk, a hard disk, etc., and the program is executed by a computer to achieve the above functions. For example, the program is stored in a memory of the device, and when the program in the memory is executed by the processor, all or some of the above functions can be implemented. In addition, when all or some of the functions in the above embodiments are implemented by means of a computer program, the program may also be stored in a storage medium such as a server, another computer, a magnetic disk, an optical disk, a flash disk or a mobile hard disk, may be saved to a memory of a local device by downloading or copying, or may perform version updating on the system of the local device. When the program in the memory is executed by the processor, all or some of the functions in the above embodiments can be implemented.

The present disclosure has been described with reference to specific examples, which are merely for the purpose of facilitating understanding of the present disclosure and are not intended to limit the present disclosure. It will be apparent to those skilled in the art that changes may be made to the specific embodiments described above in accordance with the teachings of the present disclosure.

What is claimed is:

1. A display screen switching method for a monitor which comprises a host comprising a controller, a memory, a parameter module, and a first display communicatively connected to the host, the first display being a local display of the monitor, wherein the controller of the monitor controls display screen switching between the first display and a second display external of the monitor, the display screen switching method comprising:
    displaying, on the first display, first frame data corresponding to one or more first physiological parameters according to a first display file, the first display file being stored in the memory and specifying the one or more first physiological parameters and information of a first interface layout and first interface elements based on the first display;
    detecting, by the controller of the monitor, whether the second display is connected to the monitor;
    in response to detecting that the second display is connected, further determining, by the controller of the monitor, whether a first display screen switching instruction is received, the first display screen switching instruction being generated based on an operation or a gesture of a user;
    in response to determining that the first display screen switching instruction is received:
        acquiring, by the controller of the monitor, a second display file from the memory of the monitor or the second display, the second display file specifying one or more second physiological parameters and information of a second interface layout and second interface elements based on the second display;
        acquiring data of the one or more second physiological parameters specified by the second display file from the parameter module of the monitor;
        generating, by the controller of the monitor, second frame data using the data of the one or more second physiological parameters according to the second display file;
        controlling to display, by the controller of the monitor, the second frame data on the second display external to the monitor; and
        controlling the first display to turn into a black screen when the second display displays the second frame data corresponding to the one or more second physiological parameters;
    during the second frame data being displayed on the second display, determining whether a second display screen switching instruction is received on the first display that has been turned into the black screen; and
    in response to determining that the second display screen switching instruction is received:
        acquiring data of the one or more first physiological parameters specified by the first display file from the parameter module of the monitor;
        generating, by the controller of the monitor, third frame data using the data of the one or more first physiological parameters according to the first display file;
        controlling to turn on the first display that has been turned into the black screen to display the third frame data on the first display; and
        controlling the second display to turn into a black screen when the first display displays the third frame data.

2. The display screen switching method of claim 1, wherein controlling the first display to turn into the black screen comprises turning off a backlight of the first display.

3. The display screen switching method of claim 1, wherein the first display screen switching instruction includes one of:
    a first input of touching a touch screen on the first display or a touch screen on the second display;
    a second input based on a physical operation key on the monitor or on the second display; or
    a first gesture photographed by a photographing device.

4. The display screen switching method of claim 1, further comprising:
    in response to determining that the second display screen switching instruction is received:
        generate the third frame data corresponding to the one or more first physiological parameters according to the first display file; and
        simultaneously outputting the third frame data to the first display and outputting the second frame data to the second display.

5. The display screen switching method of claim 1, wherein the first display or the second display comprises a touch screen, and the first display screen switching instruction is generated by the user touching the touch screen.

6. The display screen switching method of claim 5, wherein the touching on the touch screen includes sliding, tapping, zooming, or dragging on the touch screen.

7. The display screen switching method of claim 1, wherein the first display or the second display comprises a photographing device, and the first display screen switching instruction is generated by a second gesture photographed by the photographing device.

8. The display screen switching method of claim 7, wherein the second gesture includes sliding, zooming, or a static gesture of finger.

9. The display screen switching method of claim 1, wherein the first display screen switching instruction is generated by the user operating an operation key provided on the monitor.

10. The display screen switching method of claim 1, wherein a size of the first display is smaller than a size of the second display, and the monitor is a portable monitor.

11. The method of claim 1, wherein:
    determining that the first display screen switching instruction is received comprises detecting a first user activity, and determining that the second display screen switching instruction is received comprises detecting a second user activity, the second user activity being different from the first user activity.

12. The method of claim 11, wherein:
the first user activity is a hand movement in a first direction; and
the second user activity is a hand movement along a second direction, the second direction being a reverse direction of the first direction.

13. The method of claim 11, wherein:
the first user activity is a third gesture pointing to the first display; and
the second user activity is a fourth gesture pointing to the second display.

14. A display screen switching method for a monitor which comprises a host comprising a controller and a memory, a parameter module, and a first display, the host being coupled to the first display and being configured to couple to a second display that is an external display of the monitor, a size of the first display being smaller than a size of the second display, and the controller of the monitor controlling display screen switching between the first display and the second display, wherein the method comprises:
 displaying, on one of the first display or the second display, first frame data according to a display file of the one of the first display or the second display, the one of the first display or the second display being an original display;
 receiving a first display screen switching instruction, the first display screen switching instruction being generated based on an operation or a gesture of a user; and
 in response to receiving the first display screen switching instruction:
  identifying, by the controller of the monitor, another one of the first display or the second display as a target display;
  acquiring, by the controller of the monitor, a target display file corresponding to the target display from the memory of the monitor, the target display file specifying one or more target physiological parameters and information of an interface layout and interface elements based on the target display;
  acquiring data of the one or more target physiological parameters specified by the target display file from the parameter module of the monitor;
  generating, by the controller of the monitor, second frame data using the data of the one or more target physiological parameters according to the target display file; and
  controlling to display, by the controller of the monitor, the second frame data on the target display; and
 during the second frame data being displayed on the target display, determining whether a second display screen switching instruction is received; and
 in response to determining that the second display screen switching instruction is received:
  acquiring data of one or more original physiological parameters specified by an original display file from the parameter module of the monitor, the original display file being stored in the memory and specifying the one or more original physiological parameters and information of an interface layout and interface elements based on the original display;
  generating, by the controller of the monitor, third frame data using the data of one or more original physiological parameters according to the original display file; and
  controlling to display the third frame data on the original display.

15. The method of claim 14, wherein:
the second display screen switching instruction is identical to the first display screen switching instruction.

16. A monitor, comprising:
a first display;
a first interface circuit configured to couple the first display with a host;
a second interface circuit configured to couple a second display with the host through a pluggable interface, the second display being an external display of the monitor;
a parameter module; and
the host comprising a controller and a memory, the controller of the monitor being configured to control display screen switching between the first display and the second display external of the monitor,
wherein:
 the memory is configured to store a first display file corresponding to the first display and a second display file corresponding to the second display, the first display file specifying one or more first physiological parameters and information of a first interface layout and first interface elements based on the first display, and the second display file specifying one or more second physiological parameters and information of a second interface layout and second interface elements based on the second display; and
 the controller is configured to:
  determine whether the second display is connected to the monitor;
  in response to detecting that the second display is connected, further determine whether a first display screen switching instruction or a second display screen switching instruction is received, the first display screen switching instruction and the second display screen switching instruction being generated based on an operation or a gesture of a user, respectively;
  in response to receiving the first display screen switching instruction, acquire the first display file from the memory, output first frame data corresponding to the one or more first physiological parameters to the first display, and identify the first display to be an original display and the first frame data to be original frame data; and
  in response to receiving the second display screen switching instruction, acquire the second display file from the memory or the second display, acquire data of the one or more second physiological parameters from the parameter module of the monitor to generate second frame data according to the second display file, output the second frame data to the second display, and identify the second display to be an original display and the second frame data to be original frame data; and
  during the original frame data being displayed on the original display, determine whether a third display screen switching instruction is received; and
  in response to determining that the third display screen switching instruction is received:

identify one of the first or second display other than the original display to be a target display;

acquire data of one or more target physiological parameters specified by a target display file from the parameter module of the monitor, the target display file and the one or more target physiological parameters corresponding to the target display;

generate third frame data using the data of one or more target physiological parameters according to the target display file; and control to display the third frame data on the target display.

17. The monitor of claim 16, wherein the controller is further configured to perform at least one of:

turning the first display into a black screen when the second display displays the second frame data corresponding to the one or more second physiological parameters; or turning the second display into a black screen when the first display displays the first frame data corresponding to the one or more first physiological parameters.

18. The monitor of claim 16, wherein the first display or the second display comprises a touch screen, and at least one of the first display screen switching instruction, the second display screen switching instruction, or the third display screen switching instruction is generated by the user touching the touch screen.

19. The monitor of claim 16, wherein the first display or the second display comprises a photographing device, and at least one of the first display screen switching instruction, the second display screen switching instruction, or the third display screen switching instruction is generated by a first gesture photographed by the photographing device.

20. The monitor of claim 16, further comprising an operation panel provided with an operation key, wherein at least one of the first display screen switching instruction, the second display screen switching instruction, or the third display screen switching instruction is generated by the user operating the operation key provided on the monitor.

* * * * *